United States Patent [19]

Cho et al.

[11] Patent Number: 5,476,461
[45] Date of Patent: Dec. 19, 1995

[54] ENDOSCOPIC LIGHT DELIVERY SYSTEM

[75] Inventors: George Cho, Hopkinton; Ying H. Cho, Sudbury, both of Mass.

[73] Assignee: Cynosure, Inc., Bedford, Mass.

[21] Appl. No.: 242,308

[22] Filed: May 13, 1994

[51] Int. Cl.$^6$ .................................................. A61B 17/36
[52] U.S. Cl. ............................... 606/15; 606/17; 606/13
[58] Field of Search .............................. 606/7, 14–17, 606/2, 3, 13; 607/88, 89

[56] References Cited

U.S. PATENT DOCUMENTS

| | | |
|---|---|---|
| 4,592,353 | 6/1986 | Daikuzono . |
| 4,740,047 | 4/1988 | Abe et al. . |
| 4,773,413 | 9/1988 | Hussein et al. . |
| 4,848,339 | 7/1989 | Rink et al. ........................ 606/15 X |
| 4,860,743 | 8/1989 | Abela . |
| 4,887,600 | 12/1989 | Watson et al. . |
| 4,913,142 | 4/1990 | Kittrell et al. . |
| 4,955,882 | 9/1990 | Hakky . |
| 4,994,060 | 2/1991 | Rink et al. ........................ 606/15 X |
| 5,011,483 | 4/1991 | Sleister . |
| 5,061,266 | 10/1991 | Hakky . |

(List continued on next page.)

FOREIGN PATENT DOCUMENTS 2826383 12/1979 Germany .

OTHER PUBLICATIONS

McNicholas, T. A., et al., "Interstitial Laser Coagulation of the Prostate: Experimental Studies," *SPIE*, 1421:30–35 (1991). (From *Proceedings of Lasers in Urol., Laparoscopy, and General Surgery*, Jan. 21–23, 1991).
Moretti, Michael, "Lasers Improve Prostatectomy Treatment," Medical Laser Buyers Guide, 94–96 (1992).
Moretti, Michael, "Holmium Boosts Orthopedic Laser Development," Medical Laser Buyers Guide, p. 93 (1992).
Costello, Anthony J., et al., "Nd:YAG Laser Ablation of the Prostate as a Treatment for Benign Prostatic Hypertrophy," *Lasers in Surgery and Medicine*, 12:121–124 (1992).
Kandel, Laurence B., M.D., et al., "Transurethral Laser Prostatectomy in the Canine Model," *Lasers in Surgery and Medicine*, 12:33–42 (1992).
McCullough, David L., M.D., "Transurethral Laser Treatment of Benign Prostatic Hyperplasia," and Transurethral Ultrasound–guided Laser–Induced Prostatectomy (TULIP Procedure): A Canine Prostate Feasibility Study, by Roth, Robert A. M.D., et al., *The Journal of Urology*, 146:1126–1135 (1991).
"The Laser TURP Advantage," Intra–Sonix, Inc. pp. 1–4 (1991).
"Lasers Battle for Prostatectomy Market," Medical Laser Industry Report, 5:1–3 (Aug., 1991).
Watson, G. M., MS, "Minimally Invasive Therapies of the Prostate," *Minimally Invasive Therapy*, 1:231–240 (1992).
U.S. Patent Application Serial No. 08/049,136 filed on Apr. 19, 1993 by Krishna M. Bhatta entitled "Surgical Device and Method."

*Primary Examiner*—Stephen C. Pellegrino
*Assistant Examiner*—Michael Peffley
*Attorney, Agent, or Firm*—Hamilton, Brook, Smith & Reynolds

[57] ABSTRACT

An endoscopic light delivery system for delivering light to tissue includes a laser source for generating light. Fiber optics encased in a plastic buffer are optically coupled to the laser source for conveying the light generated by the laser source. A tip member secured to the fiber optics positions a mirror adjacent to the light delivery end of the fiber optics. The mirror redirects light conveyed by the fiber optics in a direction lateral to the fiber optics. A heat resistant ring encircling the fiber optics near the light delivery end shields the fiber optics from heat to prevent the plastic buffer near the light delivery end from melting. A lateral extension of the tip member spaces the mirror and fiber optics away from tissue. A band with a circumferential groove encircles the light receiving end of the fiber optics. A connector having a bore is capable of receiving the light receiving end of the fiber optics in the bore and locking the band within the bore by engaging the groove with a locking device.

3 Claims, 2 Drawing Sheets

U.S. PATENT DOCUMENTS

| | | |
|---|---|---|
| 5,147,353 | 9/1992 | Everett . |
| 5,151,097 | 9/1992 | Daikuzono . |
| 5,163,935 | 11/1992 | Black et al. . |
| 5,193,526 | 3/1993 | Diakuzono .......................... 606/15 X |
| 5,201,731 | 4/1993 | Hakky . |
| 5,207,672 | 5/1993 | Roth et al. . |
| 5,242,437 | 9/1993 | Everett et al. ........................... 606/15 |
| 5,242,438 | 9/1993 | Saadatmawesh et al. ............ 606/17 X |
| 5,308,311 | 5/1994 | Eggers et al. ......................... 606/29 X |
| 5,354,294 | 10/1994 | Chou ..................................... 606/17 X |
| 5,366,456 | 11/1994 | Rink et al. . |

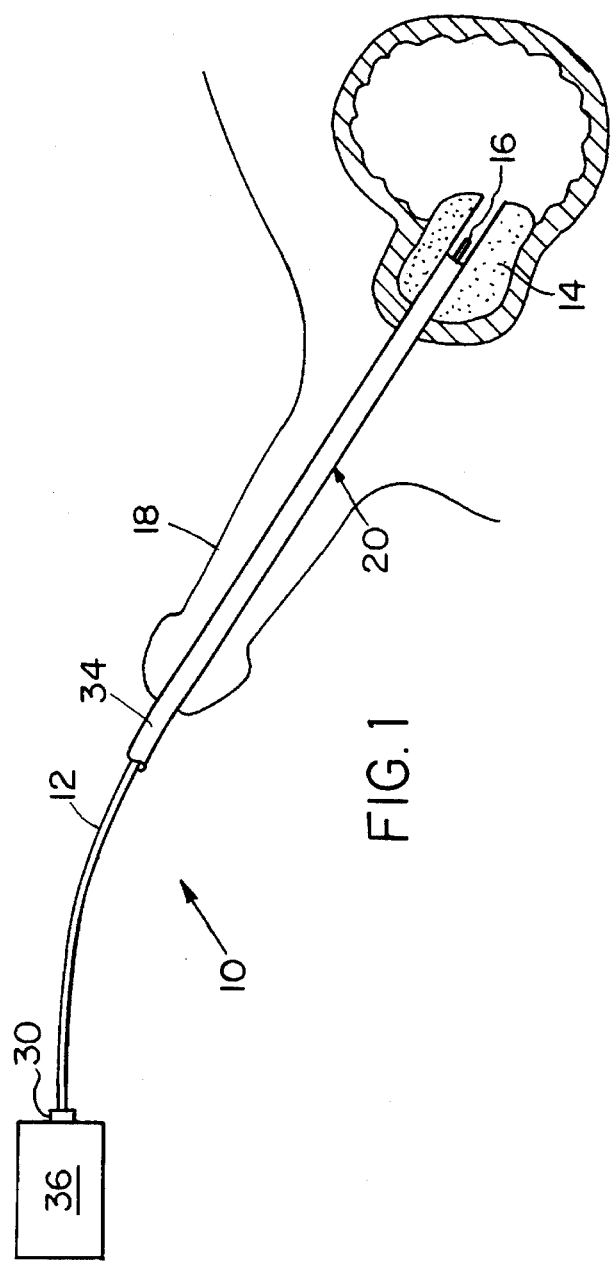
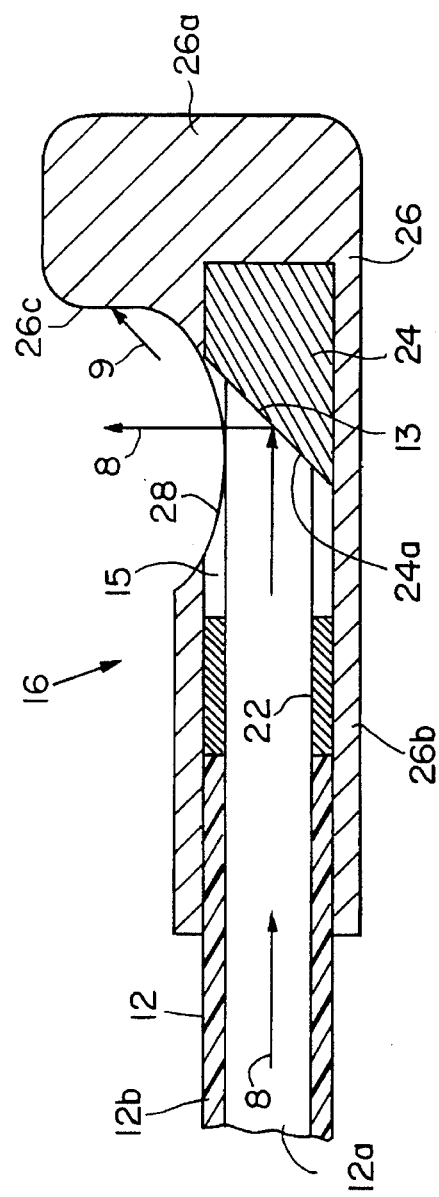

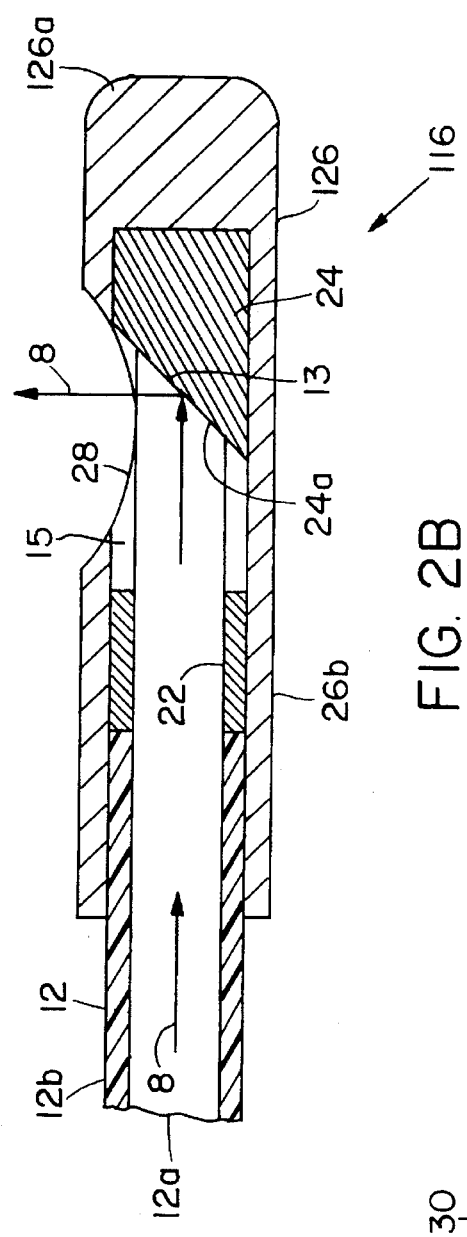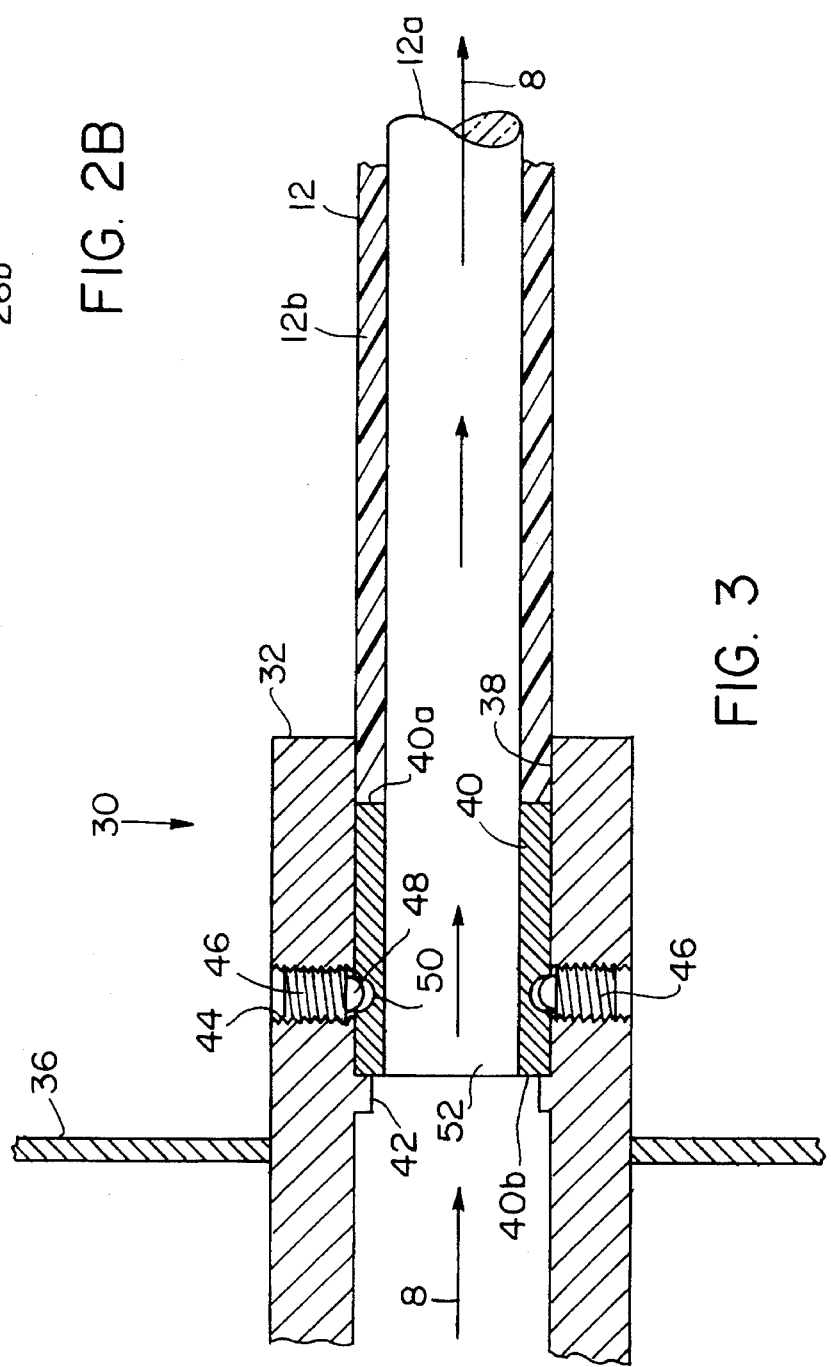
FIG. 2B
FIG. 3

ENDOSCOPIC LIGHT DELIVERY SYSTEM

BACKGROUND

Endoscopic surgery is often used to perform prostate, intra-uterine, bladder and urinary track surgery. The most common method of performing prostate surgery is to resect the enlarged prostate gland with an electrosurgical loop inserted into the urethra through an endoscope. The electrosurgical device shaves off small pieces of prostate tissue in order to enlarge the passageway, thereby providing the patient with relief. A problem with this method of surgery is that substantial bleeding occurs as the prostate tissue is being cut, making visibility through the endoscope difficult. Blood loss also complicates the surgical operation and lengthens the hospital stay. Additionally, this method of surgery is difficult to perform making extensive training necessary. Finally, the procedure is lengthy, taking up to 1½ hours to perform.

Another method of performing prostate surgery is to insert an optical fiber which is optically coupled to a laser into the prostate gland through an endoscope. The laser energy conveyed by the optical fiber coagulates or cooks surrounding prostate gland tissue. In some instances, it is desirable for the optical fiber to include a tip which directs the laser energy laterally in order to make the procedure easier to perform. The coagulated tissue remains in place for about four to six weeks before the coagulated tissue falls off and is passed during urination. Therefore, the patient must endure a long period of discomfort land may need a catheter for passage of urine until the coagulated tissue is finally passed.

Another problem with performing prostate surgery with a laser is that current fiber optics having tips for directing light laterally are easily damaged during use. One common fiber optics tip for directing light laterally has an end which is polished at an angle. The polished surface has a reflective Coating for reflecting light conveyed by the fiber optic laterally with respect to the optical fiber. A problem with the reflective coating is that if charred tissue comes in contact with the coating during surgery, the coating burns off and no longer reflects light.

Another common fiber optics tip for directing light laterally is disclosed in U.S. Pat. No. 4,740,047. This tip has a glass dome surrounding the angled polished end of the optical fiber. The problem with this tip is that as tissue is coagulated, the heated tissue pops or explodes causing shock waves which commonly break the glass dome leaving pieces of glass within the patient.

SUMMARY OF THE INVENTION

Accordingly, there is a need of a laser procedure for performing prostate surgery which provides immediate relief without substantial bleeding. Additionally, there is a need for a fiber optics tip for directing light laterally which is not easily damaged during surgery.

The present invention provides an endoscopic light delivery system for coagulating and vaporizing tissue including fiber optics for conveying light. The fiber optics have a light delivery end for delivering the conveyed light. A plastic sheath or buffer encases the fiber optics beginning a short distance away from the light delivery end for protecting the fiber optics. A mirror is positioned adjacent to the light delivery end of the fiber optics for redirecting light conveyed by the fiber optics in a direction lateral to the fiber optics. A heat resistant ring encircling the fiber optics near the light delivery end shields and protects the fiber optics from heat to prevent the plastic sheath near the light delivery end from melting.

In preferred embodiments, a tip member secured to the end of the fiber optics positions the mirror adjacent to the light delivery end of the fiber optics. The tip member has an optical window through which redirected light passes. The tip member may be shaped to extend laterally toward the tissue. This serves as a guide which spaces the optical window of the tip member away from the tissue to allow fluid flow and thus minimize heating of the fiber. Heating of the lateral extension of the tip allows the lateral extension to be used for coagulating tissue.

The present invention also provides a connector for coupling fiber optics to a light source. The fiber optics have an end for receiving light. A band encircles the light receiving end of the fiber optics. The band has a circumferential groove formed therein. The connector is optically coupled to the light source and has a bore for accepting the band at the light receiving end of the fiber optics. The connector has a locking device for engaging the groove on the band to lock the light receiving end of the fiber optics within the connector. In preferred embodiments, the locking device is a spring-loaded member for engaging the groove in the band.

The present invention light delivery system provides a method for performing prostate surgery in which tissue is coagulated and vaporized speedily using the same quartz optical fiber, thereby minimizing bleeding and providing the patient with immediate relief. The present invention also provides a fiber optics tip which is not easily damaged during surgery. Additionally, the present invention provides a simple and compact low profile connector for coupling fiber optics to a laser source.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

FIG. 1 is a simplified side view of the present invention endoscopic light delivery system.

FIG. 2A is a side sectional view of the light delivery tip of the present invention.

FIG. 2B is a side sectional view of another preferred light delivery tip.

FIG. 3 is a side sectional view of a fiber optic coupled to the present invention connector.

DETAILED DESCRIPTION OF THE PREFERRED EMBODIMENTS

In FIG. 1, endoscopic light delivery system 10 includes a laser source 36 for generating light which is optically coupled to fiber optics 12 by connector 30. Laser source is preferably a diode laser having a wavelength ranging from about 980 nm to about 1,000 nm. Fiber optics 12 conveys light generated by laser source 36. Fiber optics 12 passes through endoscopic sheath 34 which includes viewing optics (not shown) for enabling the surgeon to view surgical areas. Typically, fiber optics 12 is a single optical fiber having a diameter ranging between 1 mm and 1.5 mm. Alternatively, fiber optics 12 can be a bundle of two or more optical fibers.

A light delivery tip generally indicated at 16 is optically coupled to the end of fiber optics 12 and extends from sheath 34 to deliver the light 8 (FIG. 2) conveyed by fiber optics 12 to desired surgical areas. Light delivery tip 16 directs light in a direction lateral with respect to fiber optics 12. Light delivery tip 16 can vaporize tissue if light delivery tip 16 is in contact with the tissue or coagulate tissue if light delivery tip is spaced away from the tissue.

In order to perform prostate surgery, endoscopic sheath 34 is inserted into the urethra 20 of the penis 18 so that light delivery tip 16 can be positioned within prostate gland 14. Endoscopic sheath 34 and light delivery tip 16 are maneuvered within prostate gland 14 into a position where the light emitting portion of light delivery tip 16 is spaced away from a portion of prostate gland tissue targeted for removal to coagulate the tissue. By coagulating the tissue, bleeding does not occur when the tissue is later vaporized. Spacing light delivery tip 16 away from the targeted tissue directs light on the tissue with a power density only high enough to coagulate the tissue. The light emitting portion of light delivery tip 16 is then maneuvered to be in contact with the previously coagulated tissue to vaporize the tissue of the prostate gland in order to enlarge the passageway through prostate gland 14. By contacting the tissue with the light emitting portion of light delivery tip 16, the power density of the light directed on the targeted tissue is high enough to vaporize the tissue. Since the tissue which is removed has been previously coagulated, the surgeon's vision of the surgical area through the endoscope does not become impaired because bleeding does not occur. Alternatively, the prostate tissue can be vaporized first and then later coagulated.

Referring to FIG. 2A, light delivery tip 16 includes the end portion of fiber optics 12. Fiber optics 12 has an inner optical fiber 12a having cladding (not shown) and an outer plastic buffer 12b. Buffer 12b covers optical fiber 12a for protection except near the end 13 so that the light 8 conveyed by fiber optics 12 can be directed laterally. The end 13 of optical fiber 12a is polished at an angle. A mirror 24, having a polished angled face 24a for redirecting light 8 laterally, is positioned against end 13. In the preferred embodiment, mirror 24 is made from a solid block of gold because polished gold reflects light well and does not burn. Alternatively, other suitable reflective metals can be used such as steel or silver. Additionally, although face 24a is shown to be planar at an angle of about 45°, face 24a can be otherwise angled, curved or piecewise angled to focus light 8.

A heat resistant ring 22 encircles optical fiber 12a adjacent to buffer 12b. Heat resistant ring 22 shields and protects buffer 12b from heated tissue to prevent buffer 12b from melting. Without the heat resistant ring 22, when light delivery tip 16 is brought into contact with tissue, the heat generated by the vaporizing tissue would be high enough to melt buffer 12b. Heat resistant ring 22 prevents heat from reaching the buffer 12b through the space 15 between optical fiber 12a and the walls of tip member 26. In the preferred embodiment, heat resistant ring 22 is made of a metal such as steel, aluminum, stainless steel, copper, brass and bronze. Alternatively, other suitable temperature resistant materials can be used such as ceramics.

Tip member 26 is secured to the end of fiber optics 12 and holds mirror 24 against the end 13 of fiber 12a. Tip member 26 is crimped about mirror 24 to hold mirror 24 in place. Tip member 26 has a tubular portion 26b which slips over and is bonded to heat resistant ring 22 and buffer 12b with epoxy. Tip member 26 has an opening 28 on one side to provide an optical window for light 8 redirected laterally by mirror 24. The head 26a of tip member 26 is elongated to extend in the same lateral direction in which light 8 is directed with a surface 26c for receiving stray light 9. Light absorbed by the mirror 24 and light 9 hitting surface 26c serves to heat head 26a so that head 26a can coagulate tissue at the same time that light delivery tip 16 is vaporizing tissue. The elongated head 26a also serves to space the opening 28 from the tissue to minimize heating of the fiber tip and to prevent tissue from collecting within opening 28 when light delivery tip 16 is advanced through prostate gland 14. Tip member 26 is preferably coated with polytetrafluoroethylene (PTFE) so that tissue will not stick to it. Tip member 26 is preferably made of metal such as stainless steel, copper, brass and bronze.

Referring to FIG. 2B, light delivery tip 116 is another preferred light delivery tip which is similar to light delivery tip 16 but differs in that tip member 126 has a lower profile head 126a. Head 126a is primarily heated by the light absorbed by mirror 24 to coagulate tissue in contact with head 126a.

Referring to FIG. 3, the present invention also provides a low profile connector 30 for coupling fiber optics 12 to laser source 36. With the enlarged light delivery tip 16 of FIG. 2A, the fiber is not readily inserted into an endoscope with the tip leading. Thus, a low profile connector is required to insert the fiber with the endoscope with the connector end leading. Connector 30 is coupled to laser source 36 and includes an outer tube 32 having a bore 38 through which light 8 travels. A shoulder 42 is formed within bore 38 to serve as a stop for fiber optics 12. Locking members 46 are threaded into holes 44 and extend spring-loaded balls 48 within bore 38.

The light receiving end 52 of fiber optics 12 has a metal band 40 encircling the end 52. Surface 40a of band 40 abuts buffer 12b. An annular groove 50 encircles metal band 40. In the preferred embodiment, metal band 40 is made of stainless steel, but alternatively, can be made of copper, brass, aluminum or bronze.

Fiber optics 12 is coupled to connector 30 by inserting the light receiving end 52 of fiber optics 12 into bore 38 until surface 40b of metal band 40 reaches shoulder 42. Balls 48 of locking members 46 engage groove 50 to lock fiber optics 12 within bore 38. To disconnect fiber optics 12 from connector 30, fiber optics 12 is pulled with enough force to disengage balls 48 from groove 50.

Although examples of laser types and wavelengths have been given, laser source 16 does not have to be limited to those specific wavelengths or to a diode laser. Additionally, light delivery system 10 can be used in non-endoscopic applications.

Equivalents

While this invention has been particularly shown and described with references to preferred embodiments thereof, it will be understood by those skilled in the art that various changes in form and details may be made therein without departing from the spirit and scope of the invention as defined by the appended claims.

For example, multiple laser sources can be used for generating light. Additionally, although the present invention has been described for performing prostate surgery, the present invention may be used for performing other types of surgery such as intra-uterine, bladder, urinary track and angioplasty surgery. Finally, various features of the present invention can be used in conjunction with electrocautery surgery.

What is claimed is:

1. An endoscopic light delivery system comprising:

fiber optics for conveying light, the fiber optics having a light delivery end for delivering the conveyed light;

a mirror positioned adjacent to the light delivery end of the fiber optics for redirecting light conveyed by the fiber optics in a direction lateral to the fiber optics; and a tip member for positioning the mirror adjacent to the light delivery end of the fiber optics, the tip member having an optical window through which redirected light passes, the tip member also having a lateral extension for spacing the mirror and fiber optics from tissue, the lateral extension extending laterally from the tip member only on one side of the optical window to allow fluid flow to the fiber optics.

2. A method of delivering light with an endoscope comprising the steps of:

conveying light with fiber optics, the fiber optics being encased in a sheath and having a light delivery end for delivering the conveyed light;

redirecting light conveyed by the fiber optics in a direction lateral to the fiber optics with a mirror positioned adjacent to the light delivery end;

positioning the mirror adjacent to the light delivery end of the fiber optics with a tip member, the tip member having an optical window through which redirected light passes; and spacing the mirror and the fiber optics away from tissue with a lateral extension of the tip member, the lateral extension extending laterally from the tip member only on one side of the optical window to allow fluid flow to the fiber optics.

3. An endoscopic light delivery system comprising:

fiber optics for conveying light, the fiber optics having a light delivery end for delivering the conveyed light;

a mirror positioned adjacent to the light delivery end of the fiber optics for redirecting light conveyed by the fiber optics in a direction lateral to the fiber optics;

a tip member positioning the mirror adjacent to the light delivery end of the fiber optics, the tip member having an optical window through which redirected light passes, the tip member being coated with polytetrafluoroethylene and also having a lateral extension for spacing the mirror and fiber optics from tissue, the lateral extension extending laterally from the tip member only on one side of the optical window to allow fluid flow to the fiber optics.

* * * * *